United States Patent [19]

Wunderlich et al.

[11] Patent Number: 5,614,219
[45] Date of Patent: Mar. 25, 1997

[54] ORAL ADMINISTRATION FORM FOR PEPTIDE PHARMACEUTICAL SUBSTANCES, IN PARTICULAR INSULIN

[75] Inventors: Jens-Christian Wunderlich, Heidelberg; Ursula Schick, Schriesheim; Jürgen Werry, Ludwigshafen; Jürgen Freidenreich, Schriesheim, all of Germany

[73] Assignee: Alfatec-Pharma GmbH, Heidelberg, Germany

[21] Appl. No.: 244,691

[22] PCT Filed: Dec. 4, 1992

[86] PCT No.: PCT/DE92/01009

§ 371 Date: Sep. 13, 1994

§ 102(e) Date: Sep. 13, 1994

[87] PCT Pub. No.: WO93/10767

PCT Pub. Date: Jun. 10, 1993

[30] Foreign Application Priority Data

Dec. 5, 1991 [DE] Germany ............... 41 40 186.7
Dec. 5, 1991 [DE] Germany ............... 41 40 195.6
Dec. 5, 1991 [DE] Germany ............... 41 40 178.6
Dec. 5, 1991 [DE] Germany ............... 41 40 177.8

[51] Int. Cl.$^6$ .................. A61K 9/24; A61K 9/26; A61K 9/28

[52] U.S. Cl. .................. 424/472; 424/464; 424/465; 424/468; 424/469; 424/474; 424/484; 514/774

[58] Field of Search .................. 424/472, 469, 424/484, 464, 465, 468, 474; 514/774

[56] References Cited

U.S. PATENT DOCUMENTS 4,582,719  4/1986  Kaetsu et al. .................. 427/2

FOREIGN PATENT DOCUMENTS

42432/89  9/1989  Australia.
WO85/05029  11/1985  WIPO.

*Primary Examiner*—Thurman K. Page
*Assistant Examiner*—James M. Spear
*Attorney, Agent, or Firm*—Burns, Doane, Swecker & Mathis, LLP

[57] ABSTRACT

A peroral administration form for peptidic medicaments contains the peptidic medicament, in particular insulin, distributed in a gelatine or gelatine derivate matrix, besides usual pharmaceutical excipients and additives. By selecting an appropriate gelatine, the medicament is released in the small or large intestine, so that it is no longer enzymatically decomposed by peptidases.

13 Claims, 2 Drawing Sheets

Charge distribution in Type A (acid) and Type B (alkaline) gelatins
IEP = isoelectric point

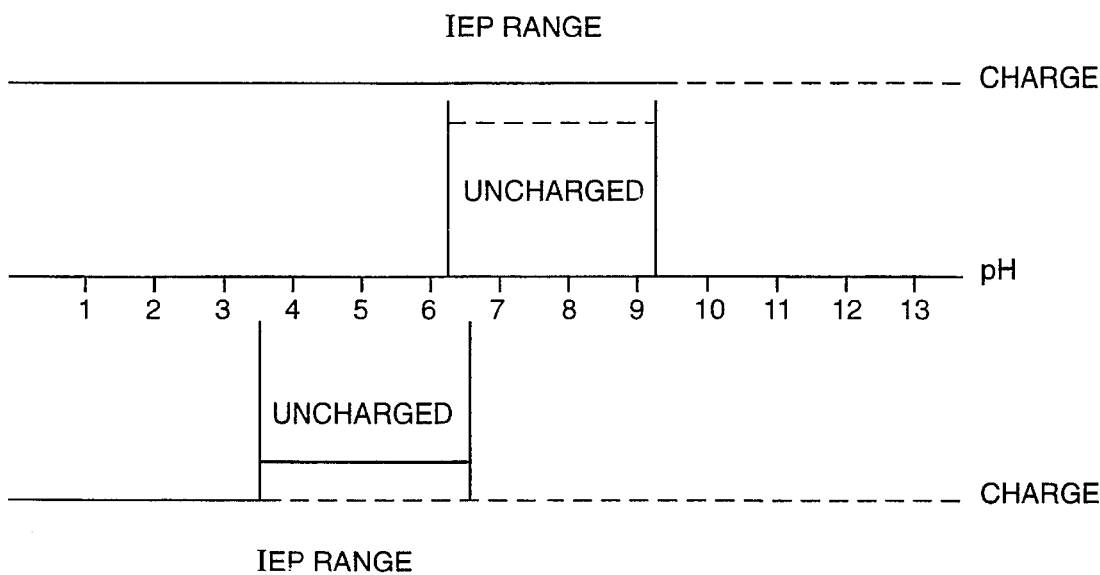
FIG._1

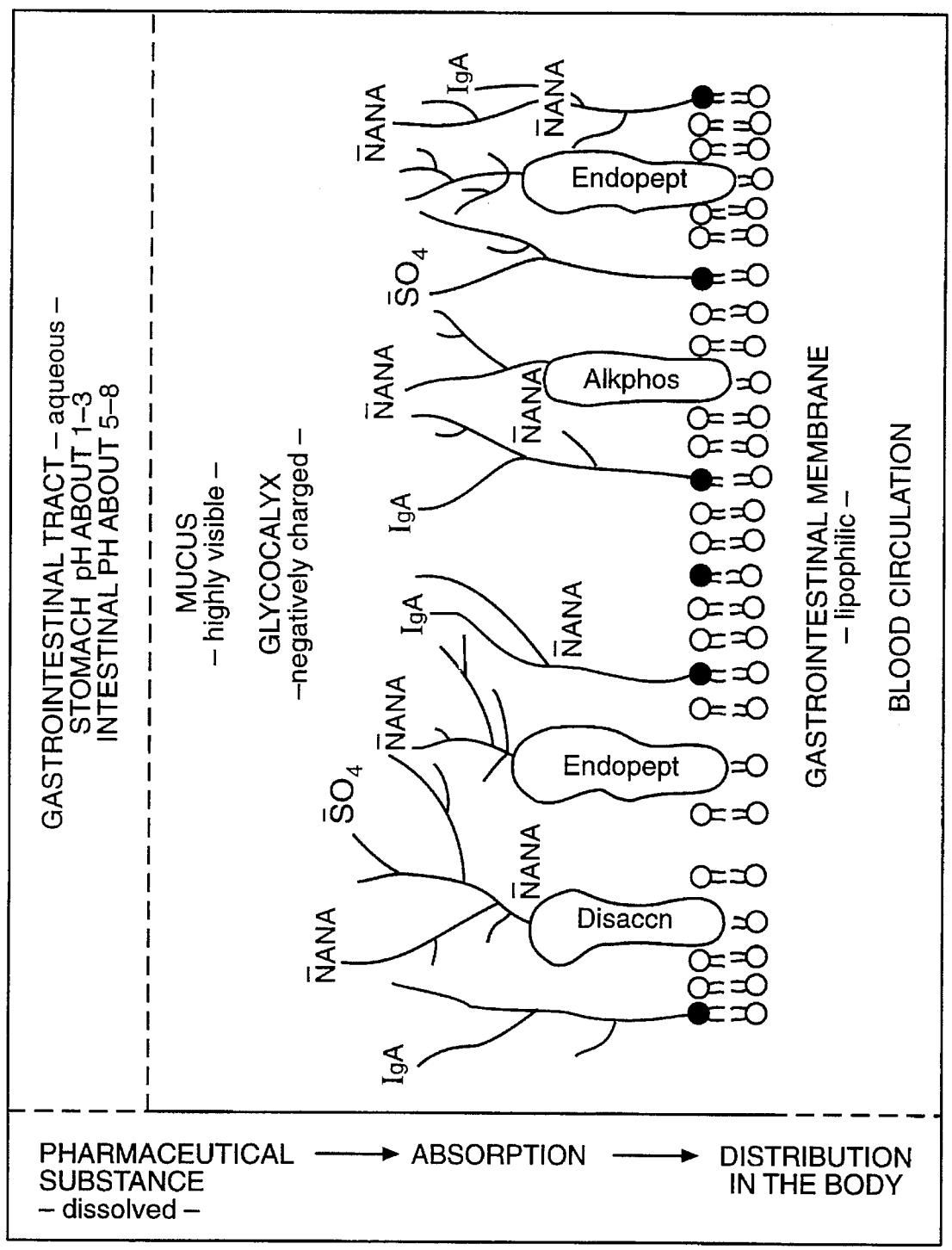
FIG._2

ORAL ADMINISTRATION FORM FOR PEPTIDE PHARMACEUTICAL SUBSTANCES, IN PARTICULAR INSULIN

The invention relates to an oral administration form for peptide medicaments, which contains at least one peptide pharmaceutical substance, dispersed in a matrix of gelatin or a gelatin derivative, in addition to pharmaceutically customary excipients and auxiliaries. The invention furthermore relates to a process for the preparation of such an oral administration form.

In the highly industrialized countries, it can be assumed that about 2–3% of the population exhibit the diabetes syndrome. For the effective treatment of this disorder with its very important symptoms hyperglycemia, polyuria, glucosuria, as well as hyperlipidemia, we have to rely today, as before, on the exogenous supply of insulin, in spite of the enormous variety of pharmaceutical developments. Even the oral antidiabetics of the sulfonylurea type, which are only indicated if the endogenous production of insulin is at least still partially maintained, at most offer a limited width of application.

The administration of insulin is carried out to the greatest possible extent by injection (parenteral administration). Other administration routes, e.g. nasal, pulmonary, rectal or, especially, oral administration are presently under test. However, it has still not become public that an appropriate preparation could be ready to be put on the market. On the contrary, we find ourselves still at the stage of informative investigations. As is known, injections are associated with disadvantages. Thus, for example, lipodystrophy or other foreign body reactions can occur at the administration site. Problems with the handling of injection syringes are particularly to be expected with very young and relatively old patients. In these groups of patients, a regularly required injection must often be carried out by a person looking after them. It is therefore obvious that this effort does not particularly promote patient compliance.

The optimum, simplest and safest use of pharmaceutical substances, however, is oral administration, for example of tablets, capsules or beverage solutions. In the case of peptide pharmaceutical substances, such as e.g. insulin, marked difficulties result, however, because these are inactivated to the greatest part by enzymatic degradation after release in the gastro-intestinal tract (GIT; stomach or small intestine) even before absorption. Enzymatic degradation in the stomach or small intestinal fluid or on the mucosa threatens to lower the bioavailability of peptide pharmaceutical substances, particularly insulin, to a minimum. Additionally, the mechanism of absorption by means of passive transport is largely lacking for peptide pharmaceutical substances. This is based, on the one hand, on the molecular size, because the exclusion limit for passive transport is assumed to be about 500 Daltons. On the other hand, substance-specific properties, such as hydrophilicity (low distribution coefficient), self-association to form larger units or binding to constituents of the gastro-intestinal tract make absorption difficult. In addition, absorption is also made difficult if negative charge formed as a result of dissociation of functional active compound groups leads to electrostatic repulsion at the glycocalyx, the negatively charged glycoprotein layer on which the lipid double layer lies. Absorption of peptide pharmaceutical substances, however, is of extraordinary importance despite this if it is wished to manage a parenteral supply successfully.

It has already been proposed to administer insulin encapsulated in liposomes. In these investigations, however, it did not appear possible to determine the amount of insulin absorbed quantitatively. These experiments can therefore probably only offer rough guiding values. The use of liposomes is moreover accompanied, as is known, by difficulties both in the preparation and in the storage of appropriate pharmaceutical forms.

More recently, useful starts were reported in order to be able to administer insulin orally. Of particular interest in this case are pharmaceutical forms which are stomach- and small intestine-resistant, and only release the insulin after reaching the colon, which is low in peptidase.

It has likewise already been proposed to introduce insulin into a soft gelatin capsule together with an absorption accelerator (EP Appl. 0 225 189), the capsule being provided with a coating which is intended to dissolve only in the colon, and the insulin being released together with said absorption accelerator. The use of absorption accelerators (e.g. certain surfactants or salicylic acid derivatives) in the GIT, however, appears only to have limited effectiveness because of the high dilution which takes place there. The very large amount which is employed for this reason, which makes up up to 50% of the capsule contents, can even cause harmful side effects. Additionally, the toxic side effects of surfactants under certain circumstances, particularly in the action on mucous membranes, are adequately known. Legitimate doubts, however, may be attached to the use of salicylic acid derivatives as pharmaceutically utilizable auxiliaries.

U.S. Pat. No. 4,849,405 proposes the embedding of insulin in a liquid, aqueous two-phase system based on a coacervate. As is known, however, coacervates do not behave in an uncritical manner during preparation. Accurate monitoring of the process parameters is unavoidable. The reproducibility of the process is therefore to be put in question. The insulin embedded in this coacervate should be a rapidly releasing pharmaceutical form, the preparation being present in liquid form (emulsion). Legitimate doubts, however, may be registered for the storage stability of this system. The coacervate can be converted into a storage-stable, delayed-release pharmaceutical form by heat treatment (curing) or by crosslinking with aldehydes (e.g. glutaraldehyde), and subsequent separation of the microcapsules by filtration and drying. In these processes, however, a loss of activity of the insulin as a result of chemical changes is not to be excluded. It is known that insulin is both sensitive to heat and is presumably hardly inert to aldehydes. Additionally, in the process indicated in U.S. Pat. No. 4,849,405 a high loss of insulin during encapsulation is generally to be expected, which is reflected with certainty in the preparation costs. Nothing is reported about the yield of the encapsulated insulin.

The present invention is now based on the object of preparing a medicament for oral administration of peptide pharmaceutical substances, in particular insulin, which overcomes the problems in this type of administration outlined in the prior art and thus makes possible a safe and effective treatment.

This object is achieved according to the invention by a medicament which contains peptide pharmaceutical substances, in particular insulin, in a gelatin matrix in addition to customary pharmaceutical excipients and auxiliaries. This object is furthermore achieved by the peptide pharmaceutical substance, in particular insulin, being associated, as a charged molecule, with an oppositely charged gelatin by adsorptive charge compensation (pseudocoacervate).

Finally, the object is also achieved by the use of a system of peptide medicaments, in particular insulin, associated by adsorptive charge compensation (pseudocoacervate) to an oppositely charged gelatin, for the production of medicaments which are suitable for the safe and effective treatment of the diabetes syndrome.

According to the present invention, for the first time an oral administration form for peptide medicaments is proposed which can be prepared and used in practice. An advantage is that the release system according to the invention is suitable both for rapid release and for delayed release or a combination of rapid release and delayed release. Furthermore, the known low absorption rate of peptide pharmaceutical substances, in particular insulin, is only significantly increased in the GIT by the present invention.

In particular, the present invention makes available an oral administration form for peptide medicaments, containing at least one peptide pharmaceutical substance in a matrix which, in addition to pharmaceutically customary excipients and auxiliaries, contains at least one hydrophilic macromolecule, selected from the group consisting of: gelatin, fractionated gelatin, collagen hydrolyzates and gelatin derivatives; and also their mixtures.

Inter alia, the present invention additionally makes available a process for the production of an oral administration form for peptide medicaments, a powdered macromolecule/pharmaceutical substance mixture being prepared using at least one hydrophilic macromolecule selected from the group consisting of: gelatin, fractionated gelatin, collagen hydrolyzates and gelatin derivatives; and also their mixtures, and the peptide medicament and the mixture being compressed.

Moreover, the present invention provides a process for the preparation of a slowly dissolving oral administration form for peptide medicaments, which comprises a) selecting a hydrophilic macromolecule selected from the group consisting of: gelatin, fractionated gelatin and gelatin derivatives; and also their mixtures, with a maximum in the molecular weight distribution in the range from about $9.5 \times 10^4 - 10^6$ D, b) converting the hydrophilic macromolecule into the sol form with water at a temperature below the inactivation temperature of the peptide, c) adjusting the pH of the sol to a value between that of the IEP of the hydrophilic macromolecule and that of the peptide, d) adding the peptide to the macromolecule sol in dissolved or undissolved form, e) removing the water, f) pressing the powder obtained to give the administration form by customary processes.

BRIEF DESCRIPTION OF THE DRAWINGS

FIG. 1 shows a schematic representation of the adjustable states of charge of gelatin as a function of the pH and IEP, it being possible for the IEP to be between 3.5 and 9.5, depending on the manner of preparation. Below pH 3.5, nearly all types of gelatin are positively charged. In the basic range above pH 9.5, all types of gelatin are negatively charged. FIG. 2 is a schematic characterizing the absoprtion process of the pharmaceutical substance into the general circulation.

The contents of the two International (PCT) Patent Applications with the titles "Pharmazeutisch applizierbares Nanosol sowie Verfahren zu seiner Herstellung" (Pharmaceutically administrable nanosol and process for its production) (81AL2730, corresponding to German Patent Application P 41 40 195.6) and "Sol-gesteuerte Thermokolloidmatrix auf Gelatinebasis für perorale Retardformen" (Sol-controlled thermocolloid matrix based on gelatin for oral sustained-release forms) (81AL2739, corresponding to German Patent Application P 41 40 192.1) by the same applicant of the same date are also made the contents of the present patent application.

Other (PCT) patent applications of ALFATEC Pharma GmbH, where appropriate also the PAZ Arzneimittelentwick-lungsgesellschaft mbH, of the same date relate to the immediate-effect form of 2-arylpropionic acid derivatives (81AL2731=German Patent Application P 41 40 185.9), the sustained-release form of dihydropyridine derivatives (81AL2732=German Patent Application P 41 40 194.8), the immediate-effect form of S- and R-ibuprofen (81AL2733=German Patent Application P 41 40 179.4), the sustained-release form of S- and R-ibuprofen (81AL2734= German Patent Application P 41 40 172.7), the immediate-effect form of S- and R-flurbiprofen (81AL2735=German Patent Application P 41 40 184.0), the sustained-release form of S- and R-flurbiprofen (81AL2736=German Patent Application P 41 40 183.2) and the sustained-release form of indolylacetic acid derivatives (81AL2737=German Patent Application P 41 40 191.3). Their disclosure is also made the subject of the disclosure of the present patent application.

In the first of the International (PCT) Patent Applications mentioned, the preparation of colloidally disperse systems (nanosols) containing gelatin is described, in the latter (81AL2737) the preparation of delayed and constant (0 order) active compound-releasing, oral pharmaceutical forms based on gelatin. Peptide pharmaceutical substances, in particular insulin, can be brought into an oral administration form according to the processes described in the patent applications mentioned. The combination of these administration forms, however, can be looked at as particularly advantageous in principle.

Insulin is a peptide pharmaceutical substance which consists of 51 amino acids which are arranged in two chains (A and B chains). Insulin is very sensitive with respect to external influences. Thus heat- and alkali-sensitivity, sensitivity to oxidizing and reducing agents, and also strongly acid-reacting substances is known. On account of its isoelectric point (IEP) of 5.3–5.4, however, insulin is adequately soluble and also adequately stable in weakly acidic medium at pH 3–4, and also in weakly alkaline medium at pH 7–8. In the pH ranges indicated, the molecule, however, is positively charged (pH less than IEP) or negatively charged (pH greater than IEP).

In a particular embodiment of the present invention which is claimed in the dependent claims, peptide pharmaceutical substances, in particular insulin, are present in a form in which the peptide pharmaceutical substance is associated in charged and simultaneously dissolved form with an oppositely charged gelatin or a gelatin derivative by adsorptive charge compensation (pseudocoacervate).

In the acidic range below pH 5.3–5.4, where the insulin molecule is positively charged, only negatively charged gelatin is suitable for this purpose. Apart from type B gelatin, certain molecular fractions of this gelatin, so-called fractionated gelatin, and also gelatin derivatives, in particular succinylated gelatin, can also be used. In the pH range indicated, these exhibit identical behavior to Type B gelatin. As one, the Type B is suitable which must have an IEP of less than 5.3–5.4 and is thus negatively charged at pHs above its IEP. Conversely, insulin is negatively charged at pHs of greater than 5.3–5.4. This negative charge can be analogously compensated only by type A gelatin which is positively charged at pHs of greater than 5.3–5.4 up to pH about 9.5.

With a pharmaceutical form prepared according to this principle, the type B gelatin is particularly to be preferred. To be precise, the following has surprisingly been shown:

After reaching the large intestine or colon, where physiological pHs of about 6–7.5 prevail and the release of insulin from the pharmaceutical form begins, the covering gelatin particles protect the insulin molecule effectively from enzymatic degradation by peptidases. At the same time, an additional effect of the gelatin further makes itself advantageously noticeable. The high molecular weight components of the gelatin (preferably from a molecular weight of about $10^7$ D) form spherically shaped networks. Diffusion of the degrading enzymes through these networks is further additionally made difficult so that the insulin molecule is even better protected. On the other hand, these gelatin particles or networks show a good adhesion to mucous membrane surfaces, which ensures optimum conditions for absorption. As a result of the pH shift to pHs of greater than 6, the insulin is now no longer present in positively charged form, but its charge is reversed and it can thus escape from the "complex" (pseudocoacervate) with the gelatin, whose charge shifts more and more into the negative range. This "charge inversion process" can additionally be accelerated according to the invention by buffer substances (e.g. disodium hydrogen phosphate) being present in the gelatin matrix whose buffer capacity maximum happens to be at pHs of greater than 6. However, it is to be stressed that in this case it is not a true inclusion complex, such as, for example, in the case of cyclodextrins. The release of insulin in each case takes place without the customary advance equilibrium, for example, with cyclodextrin compounds. Optimum conditions for the absorption of insulin in the gastrointestinal tract are thus provided.

In order to utilize this principle for an oral pharmaceutical form of insulin or alternatively other pharmaceutical substances more effectively, the pharmaceutical form described in the present invention can preferably be a two-layer tablet, or even better a layered tablet. The tablet is enteric-coated using suitable film coatings, e.g. Eudragits® (R öhm-Pharma, Germany). Eudragit S, mixtures of Eudragit S and Eudragit RS types, or mixtures of Eudragit S, Eudragit L and Eudragit RS types have proven particularly suitable. These film coatings have the advantage that they are water-impermeable up to dissolution and only begin to dissolve at pHs from about 7, i.e. after the pharmaceutical form is already in the lower intestinal sections or already in the colon. Up to this point in time, the pharmaceutical form and the active compound contained (insulin) are thus additionally effectively protected from enzymatic degradation by the enzymes of the digestive fluid.

The first layer or the coat of said pharmaceutical form is then built up such that a relatively slow (delayed) release of active compound takes place within about 4 h. The second layer, on the other hand, or the core of the layered tablet is constructed such that a rapid (non-delayed) release of active compound takes place. This combination of immediate-effect and delayed-release form in a single tablet has the advantage that the rapid release of insulin only takes place in any case after reaching the colon, where, as is known, only a low-peptidase medium is to be found.

Thus a continuous supply of the body with insulin is always provided so that an adjustment to the insulin requirement of a patient after food absorption can be easily performed. In this manner, according to the invention independence from the injection of insulin can be achieved and patient compliance can be decisively increased.

Apart from insulin, under which regular insulin, insulin complexed with zinc or alternatively globin-zinc-insulin is understood, other peptide pharmaceutical substances which can be enzymatically inactivated in the gastrointestinal tract are also suitable for the present invention, such as octreotide, desmopressin, vasopressin, triptorelin, endogenous peptide hormones, such as gonadotropin-releasing hormone, somatotropin-releasing hormone, corticotropin-releasing hormone or thyrotropin-releasing hormone, polypeptide antibiotics, cyclosporin, buserelin, calcitonin, gonadorelin, lysoprenin, oxytocin, protirelin, hirudin, glucagon, encephalin or adrenocorticotropic hormone. Substances for the treatment of AIDS (renin antagonists), treatment of hypertension (renin antagonists, enalapril, captopril, antibiotics which are derived from amino acids, penicillins (ampicillin), cephalosporins, (cefalexin), carbapenems (thienamycin), interferons (alpha-interferon) and vaccines.

The present invention additionally proposes a simple process for the production of the pharmaceutical forms described.

According to International (PCT) Application 81AL2739, a relatively viscous gelatin having an appropriate bloom number is first selected, with a maximum in the molecular weight distribution in the range $9.5 \times 10^4 – 10^6$, preferably type B with an IEP in the range from 3.5 to about 5.3, which is completely freed from foreign ions. The gelatin, which can be used for the delaying layer or the coat of the pharmaceutical form according to the invention, is first converted into the sol form with water at a temperature which is above 37° C. and below the temperature at which the insulin is already "inactivated". The gelatin concentrations are customarily 0.1–20% (percentages by weight), but preferably 0.1–5%. The pH of the sol is adjusted by addition of acid or base to a value which is above the IEP of the gelatin used and below the IEP of the insulin employed. By this means, sufficient negative charge is generated on the gelatin molecules in order to cause the adsorptive charge compensation (pseudocoacervate) with the insulin molecules. Customarily, the insulin, e.g. 50–500 I.U., can be added directly to the gelatin sol and dissolved therein with stirring or added to the gelatin sol already in dissolved form. The progressive charge compensation (pseudocoacervate formation) can be monitored here, for example, by a simple conductivity measurement of the system. It may be necessary to readjust the pH of the system to the prespecified value if this should alter during the preparation process.

The water can then be removed by known processes, such as e.g. spray- or freeze-drying, the required state of the system being fixed in dry form.

Completely analogously to this, a second, dry system is to be prepared which forms the basis for the second layer or the core of the pharmaceutical form according to the invention. The gelatin of the same type and with identical IEP used here preferably possesses a maximum in the molecular weight distribution of below $10^5$, such that a non-delayed release can be guaranteed.

The dried powders can then be pressed to give customary tablets or to give two-layer or layered tablets with the addition of customary pharmaceutical auxiliaries, such as, for example, fillers, buffer substances, flow regulators, lubricants and mold release agents. Surprisingly, the tablets according to the invention are distinguished by high breaking strength and low friability.

That layer of the two-layer tablet which is not intended to be delayed-release can be separately prepared and preisolated by coating with one of the abovementioned film-forming agents.

The customary tablets, two-layer or layered tablets prepared according to the invention are then coated by customary coating processes (for example in a fluidized bed, in a coating pan or the like) with the film-forming agents mentioned. Eudragit S is particularly advantageously used, or mixtures of Eudragit S with Eudragit RS, e.g. in a mixing ratio of 3:2.

In principle, the procedures and process variants mentioned in the abovementioned German Patent Application P 41 40 195.6 of ALFATEC-Pharma GmbH "Pharmazeutisch applizierbares Nanosol und Verfahren zu seiner Herstellung" (Pharmaceutically administrable nanosol and process for its preparation), which are referred to once more in the following, are also particularly suitable for the preparation of the administration form according to the invention:

Several processes for the preparation of the nanosols are proposed. These are an exemplary, incomplete list. The person skilled in the art can independently work out further variants in the context of the present invention on the basis of his expert knowledge:

Process I

This can be used if the pharmaceutical substance is soluble in a mixture of:
a water-miscible organic solvent and water, or several water-miscible organic solvents and water:

a) a gelatin selected in the preliminary tests is converted into sol form with water;

b) the pH of the solution found in the preliminary tests is adjusted;

c) one or more water-miscible, organic solvent(s), preferably ethanol, isopropanol or methanol, is/are added to this solution;

d) the pharmaceutical substance is added to the solution in solid form and dissolved;

e) the organic solvent(s) is/are removed, preferably by evaporating in vacuo; the nanosol is formed during the course of this;

f) the colloidally disperse solution is then dried, preferably by spray- or freeze-drying.

The organic solvent has the aim of dissolving the pharmaceutical substance and also changes the hydration shell of the gelatin molecules.

Process II

This embodiment can be used if the pharmaceutical substance is an acid or a base whose salt is soluble in water:

a) a gelatin selected in the preliminary tests is converted into the sol form with $H_2O$;

b) a pH is set which enables formation of the salt of the pharmaceutical substance;

c) the pharmaceutical substance is dissolved in the gelatin sol with salt formation;

d) by addition of alcohol or similar organic solvents, the hydration shell of the gelatin molecules can be loosened;

e) by addition of a suitable amount of acid or base, the pH is set which leads to the formation of the isoionic point (IIP) and the nanosol results;

f) the colloidally disperse solution is dried as in process I. Stage d) is optional, but preferred.

Process III

This embodiment can be used if the pharmaceutical substance is a neutral substance:

a) a gelatin sol is prepared as described in (1) a) and b).

b) a second solution is prepared from a water-miscible organic solvent, preferably ethanol, methanol, isopropanol or acetone and the pharmaceutical substance.

c) the two solutions are combined.

d) the organic solvent is removed and the colloidally disperse solution is dried.

Process IV a) As described in (I) a) and b).

b) A colloidally disperse system is briefly formed with the pharmaceutical substance, but without gelatin, in a second solution.

c) The solution obtained in (b) is continuously combined with the gelatin solution.

In step (IV) c), the continuous mixing of the solutions described in (IV) a) and b) can be controlled in a time-dependent manner by on-line measurement of the particle size using a suitable process, such as e.g. by laser light scattering (BI-FOQELS On-line Particle Sizer). It is thus possible to continuously set a desired particle size.

All processes mentioned are also suitable for collagen hydrolyzates and gelatin derivatives and can be applied without problems on an industrial scale.

The essential steps can largely run in an automated manner, it also being possible to carry out processes I to III continuously. In the case of the immediate-effect form for 2-arylpropionic acid derivatives, variants No. II and III may be mentioned as preferably suitable processes.

All gelatins, gelatin derivatives, collagen hydrolyzates and fractionated gelatin, and also their mixtures are suitable for the medicaments according to the invention. Types of gelatin which have an isoelectric point (IEP) described according to the invention which is not commercially available can be prepared according to Examples I to III from the abovementioned German Patent Application.

Compared with commercially available products, the use of gelatin which has been prepared in a special manner leads to nanosols described according to the invention having increased stability.

Examples of the preparation of grades of gelatin particularly suitable according to the invention are given below.

Examples of the Preparation of Particularly Suitable Types of Gelatin According to the Invention With Isoelectric Points Of 3.5 to 9.5

Example I

Process for obtaining an IEP of 7.5 to 9.5

Collagen-containing starting material such as e.g. pig skins is treated for 12 to 20 hours with an aqueous solution of a 0.45N mineral acid, preferably sulfuric acid, in a liquor ratio of 1:1. The excess of acid is then removed by washing several times, it being possible to use sodium hydrogen carbonate to shorten the process. The extraction of the stock-rich material is carried out using hot water at 55°–80° C. at a pH of 2.5 to 4.5. At pHs below 3.5, an IEP of 8.5 to 9.5 can be achieved, at pHs above 3.5, the IEP is 7 to 8.5.

In this manner, various IEPs from 7 to 9.5 can be achieved as a direct function of the pH during the extraction.

After the extraction process step, the aqueous solution is neutralized and worked up as customary.

Depending on the temperature selected during the extraction, types of gelatin having high to medium molecular weight distributions can furthermore be obtained by this process.

At temperatures of 50°–55° C., particularly highly viscous and high-bloom grades are obtained. Types of gelatin having low molecular weight or cold water-soluble gelatins can be obtained by controlled degradation with collagenases.

Example II

Process for achieving an IEP of 4 to 7.5

The collagen-containing starting material is first washed to remove foreign substances and comminuted, and then homogeneously rendered alkaline by addition of magnesite, sodium hydroxide solution or calcium hydroxide by thorough mixing in the liquor ratio 1:1.2. The material pretreated in this way is briefly hydrolyzed by pressure hydrolysis at $1.01 \times 10^5$ to $2.02 \times 10^5$ Pa and a pH of the aqueous solution of 8–14. After hydrolysis, it is immediately neutralized and the still hot aqueous gelatin solution is filtered, deionized, concentrated and dried in the usual manner.

If a weakly basic hydrolyzing agent such as magnesite is taken, an IEP of 6 to 7.5 is obtained if the reaction is carried out at $1.01 \times 10^5$ Pa. IEPs of 5 to 6 are obtained when using a dilute milk of lime suspension, and when using 0.005 to 0.1N sodium hydroxide solution IEPs of 4 to 5 can be achieved.

Types of gelatin having a low degree of racemization and a low peptide content can be obtained with pressure ratios of $1.01 \times 10^5$ Pa and residence times of at most 10 min.

Medium to low molecular weight types to cold water-soluble types are afforded by correspondingly longer residence times.

Example III

Process for Achieving an IEP of 3.5 to 6

Collagen-containing starting material, preferably split or ossein, is subjected after the starting wash to treatment with a high-speed asher. In this case, two process variants in the liquor ratio 1:1.3 offer themselves, which either use a saturated milk of lime suspension or a 0.1 to 1N sodium hydroxide solution.

When using a milk of lime suspension, the raw material is hydrolyzed for a maximum of 3 to 4 weeks with continuous agitation. The material is then neutralized by addition of acid and washed several times. Further working up follows in the usual manner. IEPs of 4 to 6 can be set in this manner.

When using sodium hydroxide solution, the asher process can be shortened again, the material, depending on the degree of comminution, being hydrolyzed even after 6–12 hours at concentrations of 1N sodium hydroxide solution. Neutralization is carried out using equimolar amounts of mineral acid and the neutral salts are removed by washing several times or by deionizing the aqueous gelatin solution obtained in the extraction. In this process variant, IEPs of 3.5 to 5 can be obtained.

Particularly low-peptide types of gelatin are obtained with a short residence time in the asher. Types of gelatin with high to average molecular weight distribution ($M=10^4$–$10^7$ D) can thus be obtained.

Low molecular weight to cold water-soluble types of gelatin can be obtained by thermal degradation or enzymatically.

Depending on the gelatin preparation procedure (extent of degredation of native collagen and acidic or alkaline hydrolysis process), gelatin of Type A or Type B has a characteristic molecular weight spectrum or molecular weight distribution. Table 1 indicates the molecular weight distributions of various types of gelatin or of collagen hydrolyzates, and the percentage content (frequency) of individual molecular weight ranges.

TABLE 1

Molecular weight distribution of various known types of gelatin or of known collagen hydrolyzates

| Molecular Mass Distribution (kD) | Native Collagen % | Gelatin Type B % | Gelatin Type A % | Collagen hydrolyzate Gelita ® Collagel A | Collagen hydrolyzate Gelita ® Collagel B | Collagen hydrolyzate Gelita ® Sol C | Elastin hydrolyzate Gelita ® Gelatin |
|---|---|---|---|---|---|---|---|
| >360 | 100 | 28.0 | 18.0 | 0 | 0 | 0 | 0 |
| 285 | 0 | 7.0 | 9.0 | 0 | 0 | 0 | 0 |
| 145–237 | 0 | 20.0 | 34.0 | 1.0 | 1.5 | 0 | 0 |
| 95 | 0 | 26.0 | 11.0 | 0 | 0 | 0 | 0 |
| 95–50 | 0 | 16.3 | 13.4 | 2.6 | 4.0 | 1.1 | 0 |
| 50–20 | 0 | 7.4 | 9.1 | 13.0 | 14.5 | 0.3 | 0 |
| 20–10 | 0 | 3.9 | 3.8 | 43.0 | 31.5 | 3.7 | 0.2 |
| 10–5 | 0 | 3.0 | 3.0 | 25.4 | 20.0 | 12.2 | 5.2 |
| 5–2 | 0 | 0 | 0 | 6.0 | 14.0 | 26.0 | 93.9 |
| 2–1 | 0 | 0 | 0 | 7.0 | 8.0 | 23.0 | 0 |
| <1 | 0 | 0 | 0 | 6.3 | 7.0 | 34.0 | 0 |
| MW | 360 | 165 | 185 | 12–18 | 12–18 | 3 | 2–3 |

The predominance of an individual range compared with the other molecular weight ranges of the same gelatin can be seen clearly in the individual columns. This range is thus the maximum in the molecular weight distribution (it is 95 kD e.g. for the Type B gelatin shown in the figure). The concept of the "maximum of the molecular weight distribution", however, is to be separated strictly from the concept of the "average mean molecular weight". This mean value is 165 kD for the gelatin of Type B mentioned.

Customary pharmaceutical auxiliaries and/or other macromolecules, if they are technologically necessary, can be added to the nanosols according to the invention in the liquid or dry state.

For example, an addition of polyvinylpyrrolidone in the quantitative ratio gelatin to polyvinylpyrrolidone in the range from 5:1 to 500:1 may be suitable.

The technological processing properties of an immediate-effect form within the meaning of the invention, which is processed e.g. to give tablets or is to be lyophilized, can be improved by addition of low molecular weight types of polyvinylpyrrolidone in the range 10:1 to 50:1 without the stability of the nanosols being adversely affected.

The preferred preparation processes, procedures and names in the following examples relate as follows to the German Patent Application "Pharmazeutisch applizierbares Nanosol und Verfahren zu seiner Herstellung" (Pharmaceutically administrable nanosol and process for its preparation) (P 41 40 195.6) or the abovementioned processes and examples:

Nanosol preparation: Processes II and III
Gelatin preparation: Examples I to III
Preliminary test: see the following description:
Preliminary test:

As already mentioned at the beginning and as is evident from FIG. 1, the absolute, maximum possible net charge of an individual gelatin molecule depends mainly on the number of free COOH and $NH_2$ groups and the pH of the solution. As Type A, B, collagen hydrolyzates or gelatin derivatives differ in the number of free COOH groups, their maximum possible net charge is thus also different. With gelatin derivatives, the state of charge can additionally depend on the type of modification.

When carrying out the process according to the invention, the suitable gelatin and the suitable pH are selected in a preliminary test.

First, a working pH range suited to the physicochemical properties of the pharmaceutical substance is selected. Physicochemical properties of the pharmaceutical substance to be taken into account in particular are: the solubility (in organic solvents or water), its properties as an acid, base or neutral substance and its stability to acids and alkali solutions.

In a first rapid test, it is determined what charge the precipitated particles have. This results, taking into account the working pH range, in the choice of a suitable type of gelatin. If the particles are, for example, negatively charged, a gelatin is picked which is positively charged under the given pH conditions. This rapid test for the determination of the particle charge has the advantages that it can be carried out without a great outlay in terms of apparatus and time. A time-consuming and inaccurate zeta potential measurement can thus be dispensed with entirely.

In many cases, it will be adequate for this rapid test to convert two commercially available Type A and B gelatins with an IEP of 9.5 or 3.5 respectively and with peptide contents of<30% and a bloom number of 200, which are additionally designated as standard gelatins, into the sol form at a pH of 6 (5% strength aqueous solution) and to dissolve the pharmaceutical substance in a water-miscible solvent, such as e.g. ethanol, isopropanol or acetone, and in each case to mix homogeneously with the gelatin solutions. At the same dose of the pharmaceutical substance, in the case of the gelatin which is unsuitable in its state of charge a colloidal system will either not form or immediately become unstable or the pharmaceutical substance will flocculate. If the resulting particles are negatively charged, they are stabilized earlier by the gelatin solution of Type A, which is positively charged at a pH of 6, than by the solution containing Type B gelatin; in contrast, in this case Type B either will form no colloidal system or the system will immediately destabilize. The flocculation of the particles can be monitored e.g. via a simple turbidity measurement.

In this rapid test, the working pH range must be taken into account in each case. Other gelatins can also be selected as a standard, but they must be selected in their IEP such that they carry an opposite net charge at this pH (see also FIG. 1). In most cases, said standard Type A and B gelatins are adequate for this rapid test.

Starting from the result of the preliminary experiment, the optimum conditions for the formation of the nanosols are determined by stepwise variation of the IEP by use of appropriate types of gelatin and of the pH of the solution in relatively small ranges (e.g. 0.1 pH steps), i.e. the stability optimum which is characterized by the isoionic point (IIP) must be found in order to guarantee an adequate stability for the pharmaceutical applications mentioned.

It can definitely be the case that a stability of the nanosols which is acceptable within the meaning of the invention is already found in a relatively narrow pH range (about 0.5 units) around the isoionic point, so an adjustment of this point itself is not absolutely necessary. On the other hand, several gelatins can also lead to the same, stable results. Thus, for example (Example 5) with the oral antidiabetic glibenclamide in the case of a Type B gelatin with an IEP of 5.5 the stability optimum can be at a pH of 3.2, while in the case of a Type B gelatin with an IEP of 3.8 the stability optimum is at a pH of 2.2.

Characterized by a stability maximum, in both cases the isoionic point was reached (the dependence of the net charge on the pH and the IEP must be non-linear, as it is given by the $pK_a$ value of the COOH or $NH_3^+$ groups present).

The two systems described for the delayed and non-delayed release of insulin can also be shaped by suitable granulation methods to give granules or conventional pellets. Such granules or pellets can be filled, for example, into hard gelatin capsules. Granules, pellets and hard gelatin capsules are customarily coated with the same film-forming agents as indicated for the tablet according to the invention in order to achieve at least a resistance to gastric juice. In this manner, for example, mixtures of rapid- and delayed-release pellets can be realized in a single pharmaceutical form (hard gelatin capsules), it being possible for the types of pellet to be additionally coated with various film-forming agents. It is thus possible to carry out the adjustment to the insulin requirement of the body even more accurately, as is already possible anyway with a tablet.

Oral pellet pharmaceutical forms are furthermore distinguished in that in their gastrointestinal transit times they are substantially more independent of physiological effect factors, such as e.g. the nature and amount of food absorbed among other things, as single-unit pharmaceutical forms such as e.g. tablets.

The oral pharmaceutical forms described in the present patent application can also be employed advantageously for other administration routes.

Thus a tablet according to the invention, in particular a simple sustained-release preparation can be used for the administration of peptide pharmaceutical substances in the oral cavity (buccal or sublingual). The bioadhesive properties of the gelatin in this case cause adhesion to the oral mucous membrane after contact with physiological fluid.

According to the invention, spray- or freeze-dried powders can be advantageously employed for the development of nasal sprays or nasal gels (nasal administration). After insufflating into the nasal cavities, the gelatin/pharmaceutical substance particles adhere to the nasal mucous membrane as a result of bioadhesive properties and exhibit a residence period in the nose of on average 3 to 4 hours.

In order to explain the physiological background of the absorption of pharmaceutical substances in general and the improved absorption rate of the nanosols or pseudocoacervates according to the invention adequately, first a consideration of the mechanism of physiological absorption of pharmaceutical substances, as is also presented in relevant publications, is necessary. However, the present invention is neither tied to the following attempt at a scientific explanation of the phenomena occurring according to the invention nor can it be restricted by this.

Passive pharmaceutical substance absorption takes place according to the present state of knowledge (theory according to Brodie et al.), if the following conditions exist:

a) the gastrointestinal membrane acts as a lipid barrier, b) the pharmaceutical substance is only absorbed in dissolved and uncharged, i.e. nonionized form, c) acidic pharmaceutical substances are preferably absorbed in the stomach and basic pharmaceutical substances preferably in the intestine.

After the oral uptake of a pharmaceutical substance into the body, its absorption, i.e. the crossing into the general circulation (biophase) is prevented to a great degree by physical barriers (see FIG. 2), namely by the mucus layer and an aqueous layer adhering thereto the cell membranes of the intestinal epithelial cells with the glycocalyx covalently bonded thereto and the so-called "tight junctions" which connect the epithelial cells with one another on their apical side.

These barriers presuppose that absorption of pharmaceutical substances takes place through the lipid double layers fundamentally independently of their distribution mechanism and state of charge (so-called passive diffusion).

The epithelial cells of the entire gastro-intestinal tract are covered with a mucus layer which consists of mucins (glycoproteins), electrolytes, proteins and nucleic acids. In particular, the glycoproteins form with the main component of mucus, namely water, a viscous gel structure which primarily performs protective functions for the underlying epithelial layer. The mucus layer is bound to the apical surface of the epithelial cells via the glycocalyx. The glycocalyx likewise has a glycoprotein structure which is covalently bonded to components of the membrane double layer of the epithelial cells. The branched polysaccharides of the glycocalyx, which are either directly covalently bonded to amphiphilic molecules of the double membrane or to the proteins incorporated in the double membrane, possess charged N-acetylneuraminic acid and sulfate radicals and are therefore negatively charged, which can lead to an electrostatic bond or repulsion of charged pharmaceutical substance molecules or of electrostatically charged particles respectively. The epithelial cell membranes consist of phospholipid double layers in which proteins are anchored via their hydrophobic regions. The phospholipid double layers with their lipophilic content represent a further barrier for the transport of the pharmaceutical substances to be absorbed.

From this description, it clearly follows that charged pharmaceutical substance molecules or electro-statically charged particles therefore only have a very low chance of being absorbed via the oral administration route.

The nanosols according to the invention for the first time provide the technical teaching to form a system with which these abovementioned obstacles to absorption can be overcome. As the active compound nanoparticles are stabilized in neutrally charged form by the gelatin according to the invention, they can be transported through the negatively charged glycocalyx without relatively great obstructions, in contrast to other described nanoparticles of the prior art, which are not or cannot be stabilized in neutrally charged form. According to the invention, the adjustment of the isoionic state of charge can additionally be effected in coordination with the physiological conditions.

As the active compound nanosols or pseudocoacervates according to the invention can pass through the glycocalyx without hindrance, without being bonded or repelled by electrostatic effects, they thus also reach the surface of the epithelial cells and are available there in a high concentration.

Active, carrier-mediated transport mechanisms or phagocytosis can then also make a substantial contribution to the absorption of the active compound nanosols.

The following examples are intended to illustrate the invention in greater detail, but without making a claim to completeness:

EXAMPLE 1

Active compound: normal insulin (German Pharmacopeia 9)

| | |
|---|---|
| IEP: | 3.5 |
| Characteristic bloom number: | 280 for delayed release<br>30 for rapid release |

500 g in each case of the gelatins specified above are converted into the sol form with distilled water at 40° such that a 5% strength solution results. A pH of 3.9 is adjusted in each sol. 30,000 I.U. each of insulin of the described specification are then dissolved in both batches. The adsorptive charge compensation (pseudo-coacervate formation) taking place is monitored by conductivity testing (e.g. using a microprocessor-controlled high performance conductometer from WTW) until a change in the total conductivity no longer occurs.

Both solutions are then converted into the dry form by separate spray-drying at an outlet temperature of the spray stream of about 45°–50° C.

Layered tablets which, as the core, possess the insulin in non-delayed form are produced in a tablet press with admixture of customary pharmaceutical auxiliaries. The unfinished tablet blanks are then coated in a coating pan by spraying on a solution of Eudragit S and Eudragit RS in the ratio 3:2 in acetone.

EXAMPLE 2

Analogously to Example 1, the dried powders are first prepared. Each powder is granulated per se with admixture of customary pharmaceutical auxiliaries and shaped to give pellets.

The pellets are then coated in a coating pan for rapid release of insulin by spraying on an acetone solution of Eudragit S and Eudragit RS in the ratio 3:2 and the pellets for sustained insulin release analogously with Eudragit S.

Both types of pellet are filled in a mixture ratio of 1:1 into hard gelatin capsules which are coated with Eudragit S after sealing.

EXAMPLE 3

| | |
|---|---|
| Active compound: | Corticotropin, IEP in the weakly alkaline range at about 8 |
| Gelatin: | Type A, completely freed from |

-continued

| | |
|---|---|
| | foreign ions. |
| IEP: | 9.0 |
| Characteristic bloom number: | 320 for delayed release |
| | 30 for rapid release |

300 g in each case of the gelatins specified above are converted into the sol form with distilled water at 40° such that a 3% strength solution results. By means of hydrochloric acid (2%), a pH of 8.5 is adjusted in each sol. 200 mg each of corticotropin of the described specification are then dissolved in both batches.

Both solutions are then converted into the dry form by separate spray-drying at an outlet temperature of the spray stream of about 45°–50° C.

Layered tablets which, as the core, possess the corticotropin in non-delayed form are produced in a tablet press with admixture of customary pharmaceutical auxiliaries.

The unfinished tablet blanks are then coated in a coating pan by spraying on a solution of Eudragit S in acetone.

We claim:

1. An oral administration form for peptide medicaments, containing at least one peptide pharmaceutical substance in a matrix of gelatin, fractionated gelatin or collagen hydrolyzate which dissolves under physiological conditions, in addition to pharmaceutically customary excipient and auxiliaries, the peptide pharmaceutical substance(s) present in colloidal or dissolved form possessing a charge and the molecules of the matrix-forming agent possessing an opposite charge wherein the gelatin has a molecular weight distribution whose maximum is at $10^4$ to $10^7$ D and wherein a layer construction is present.

2. An oral administration form for peptide medicaments, containing at least one peptide pharmaceutical substance in a matrix of gelatin, fractionated gelatin or collagen hydrolyzate which dissolves under physiological conditions, in addition to pharmaceutically customary excipient and auxiliaries, the peptide pharmaceutical substance(s) present in colloidal or dissolved form possessing a charge and the molecules of the matrix-forming agent possessing an opposite charge which is provided with a synthetic or natural coating.

3. An oral administration form for peptide medicaments as in claim 2, which is constructed as a layered tablet.

4. An oral administration form for peptide medicaments, containing at least one peptide pharmaceutical substance in a matrix of gelatin, fractionated gelatin or collagen hydrolyzate which dissolves under physiological conditions, in addition to pharmaceutically customary excipient and auxiliaries, the peptide pharmaceutical substance(s) present in colloidal or dissolved form possessing a charge and the molecules of the matrix-forming agent possessing an opposite charge wherein a time-controlled first form is combined with a second form that dissolves at a faster rate than the first form.

5. An administration form as in claim 4, wherein from the outside the first layer or the coat contains a depot form, while the second layer or the core contains an immediate-effect form.

6. A process for the production of an oral administration form for peptide medicaments, which comprises a) selecting a gelatin, fractionated gelatin, or collagen hydrolyzate according to its isoelectric point (IEP) such that its IEP is matched with the charge state of the pharmaceutical substance particles such that the gelatin leads to charge neutrality with the undissolved pharmaceutical substance at a specific pH, b) the gelatin, fractionated gelatin or collagen hydrolyzate is converted into the aqueous sol form, c) the pH is adjusted as a function of the IEP of the gelatin to such a value that the nanoparticles of the pharmaceutical substance forming are almost or completely stabilized in a neutrally charged manner, and d) before or after stage c), the pharmaceutical substance is dissolved in the aqueous sol or a solution of the pharmaceutical substances is combined with the aqueous sol.

7. A process for the production of an oral administration form for peptide medicaments, which comprises a) selecting a gelatin, or fractionated gelatin with a maximum in the molecular weight distribution in the range from $10^4$–$10^7$ D, which is free from foreign ions, wherein the gelatin has a content of microgel of greater than 10% by weight, b) converting the gelatin or fractionated gelatin into the sol form with water at a temperature above 37° C. and below the inactivation temperature of the peptide, c) adjusting the pH of the sol to a value between that of the IEP of the gelatin or fractionated gelatin and that of the peptide, d) adding the peptide in dissolved or undissolved form to the sol and optionally dissolving in the sol, e) removing the water, f) pressing the powder obtained to give the administration form by customary processes and g) optionally coating the shaped article with a film-forming agent.

8. A process for the production of an oral administration form for peptide medicaments, which comprises preparing a powdered gelatin/pharmaceutical substance mixture with a gelatin, fractionated gelatin, or collagen hydrolyzate, which dissolves in physiological medium under physiological conditions, and compressing the mixture.

9. The process as in claim 7 wherein the stages a) to e are carried out with a second gelatin or a collagen hydrolyzate which contains a maximum in the molecular weight distribution below $10^5$, and stage f) comprises pressing the two powders obtained to give two layer or layered tablets.

10. An oral administration form for peptide medicaments as in claim 2 wherein the peptide pharmaceutical substance is insulin.

11. An oral administration form for peptide medicaments as in claim 1 wherein the peptide pharmaceutical substance is insulin.

12. The process as in claim 6 wherein the pharmaceutical substance is insulin.

13. A process for the production of an oral administration form for insulin medicaments, which comprises a) selecting a gelatin, or fractionated gelatin with a maximum in the molecular weight distribution in the range from $10^4$–$10^7$ D, which is free from foreign ions, b) converting the gelatin or fractionated gelatin into the sol form with water at a temperature above 37° C. and below the inactivation temperature of the insulin, c) adjusting the pH of the sol to a value between that of the IEP of the gelatin or fractionated gelatin and that of the insulin, d) adding the insulin in dissolved or undissolved form to the sol and optionally dissolving in the sol, e) removing the water, f) pressing the powder obtained to give the administration form by customary processes and g) optionally coating the shaped article with a film-forming agent.

* * * * *